United States Patent
Kim et al.

(10) Patent No.: US 10,357,456 B2
(45) Date of Patent: Jul. 23, 2019

(54) PARENTERAL BIOACTIVE SUBSTANCE DELIVERY COMPOSITION BASED ON LOW MOLECULAR WEIGHT METHYL CELLULOSE

(71) Applicant: INDUSTRY-UNIVERSITY COOPERATION FOUNDATION HANYANG UNIVERSITY, Seoul (KR)

(72) Inventors: Yong-Hee Kim, Seoul (KR); Jang-Kyung Kim, Gyeonggi-do (KR); Jae Ho Koh, Seoul (KR)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 0 days.

(21) Appl. No.: 15/467,778

(22) Filed: Mar. 23, 2017

(65) Prior Publication Data
US 2017/0273904 A1    Sep. 28, 2017

(30) Foreign Application Priority Data

Mar. 24, 2016 (KR) .................. 10-2016-0035528
Mar. 17, 2017 (KR) .................. 10-2017-0033736

(51) Int. Cl.
| | | |
|---|---|---|
| A61K 9/107 | (2006.01) | |
| A61K 47/38 | (2006.01) | |
| A61K 31/337 | (2006.01) | |
| A61K 9/00 | (2006.01) | |

(52) U.S. Cl.
CPC .......... *A61K 9/1075* (2013.01); *A61K 9/0019* (2013.01); *A61K 31/337* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,048,433 A | * | 9/1977 | Burns | ............... C08B 11/02 510/299 |
| 5,569,483 A | * | 10/1996 | Timonen | ............... A21D 2/18 127/37 |
| 8,980,248 B2 | * | 3/2015 | Shoichet | ............... A61K 9/0024 424/93.7 |
| 2011/0257253 A1 | * | 10/2011 | Seo | ............... A61K 9/1075 514/449 |
| 2013/0189230 A1 | | 7/2013 | Shoichet et al. | |
| 2014/0031769 A1 | * | 1/2014 | de Juan, Jr. | ............... A61K 9/0051 604/294 |
| 2016/0106848 A1 | * | 4/2016 | Kim | ............... A61K 9/0024 514/9.1 |

FOREIGN PATENT DOCUMENTS

KR    10-2014-0133724         11/2014
WO    WO 2014182101 A1 *    11/2014    ........... A61K 9/0024

OTHER PUBLICATIONS

Zhang et al., Pharmaceutics, 5: 329-352 (2012).*
Kim et al., Pharm. Res., 29: 525-534 (2012).*
Huang et al., J. Phys. Chem. B, 118: 13992-14008 (Year: 2014).*
Hugouvieux et al. Soft Matter, 7: 2580-2591 (Year: 2011).*
Huang Dissertation, "Multi-scale Modeling of Cellulosic Polymer for optimal Drug Delivery Properties in Solid Dispersion Formulations" (Year: 2017).*
AntiAging Skin Care, downloaded from http://antiagingcareforwomen.com/margarine-as-skin-softener/ Jan. 3, 2018 (Year: 2007).*
Jae Ho Koh, "Studies on solubilization of insoluble drugs using low molecular weight methylcellulose", Graduate School of Hanyang University, Feb. 2016, Thesis paper, Department of Bioengineering Graduate school of Hanyang University, 43 pages.
Miyata et al., "Polymeric mecelles for nano-scale drug delivery", Reactive & Functional Polymers 71 (2011) 227-234.
Korean Office Action for 10-2017-0033736, dated Apr. 25, 2019, 5 pages (in the Korean language).

* cited by examiner

*Primary Examiner* — Susan T Tran
(74) *Attorney, Agent, or Firm* — Adsero IP

(57) ABSTRACT

The present invention relates to a parenteral bioactive substance delivery composition and a bioactive substance carrier using a micelle based on low molecular weight methyl cellulose with a weight average molecular weight of 6 to 9.5 kDa. The low molecular weight methyl cellulose with a weight average molecular weight of 6 to 9.5 kDa resolves a problem of excretion to outside of the body to improve safety and form a micelle to solubilize poorly soluble bioactive substances, and thus is very useful for sustained release parenteral bioactive substance delivery.

9 Claims, 18 Drawing Sheets

US 10,357,456 B2

PARENTERAL BIOACTIVE SUBSTANCE DELIVERY COMPOSITION BASED ON LOW MOLECULAR WEIGHT METHYL CELLULOSE

CROSS-REFERENCE TO RELATED APPLICATION

This application claims priority to and the benefit of Korean Patent Application No. 10-2016-0035528, filed on Mar. 24, 2016, the disclosure of which is incorporated herein by reference in its entirety and to Korean Patent Application No. 10-2017-0033736, filed on Mar. 17, 2017.

BACKGROUND

1. Field of the Invention

The present invention relates to a micelle particle, a parenteral bioactive substance delivery composition and a bioactive substance carrier based on low molecular weight methyl cellulose.

2. Discussion of Related Art

In the drug delivery system for solubilizing most poor-water soluble drugs to be delivered into the body, a drug delivery technology using various surfactants or additives such as alcohols, a drug delivery technology using a polymer, a drug delivery technology using a copolymer formed of two or more polymer blocks having hydrophilic and hydrophobic block properties such as PEG-PLGA and the like are mostly used [Kanjiro Miyata, R. James Christie, Kazunori Kataoka, Polymeric micelles for nano-scale drug delivery, Reactive and Functional Polymers, Volume 71, Issue 3, March 2011, Pages 227-234]

Methods of solubilizing such a poorly soluble drug have been reported to cause side effects in the nervous system and the digestive system due to adding various surfactants or additives such as alcohols for injection into the blood vessels of the body.

Furthermore, in the case of the drug delivery technology using a copolymer, problems such as lack of biocompatibility of synthetic polymers of copolymer units and a complex process have arisen. Moreover, the efficiency of discharge from the living body is reduced due to a high molecular weight.

Therefore, there is an urgent need for development of a new formulation which can use a poorly soluble drug by a drug carrier having increased biocompatibility and biodegradability without the problems as described above.

SUMMARY OF THE INVENTION

Accordingly, the inventors of the present invention developed a parenteral bioactive substance delivery composition based on methyl cellulose with a weight average molecular weight of 6 to 9.5 kDa, which is able to completely resolve the kidney toxicity problem that cannot be resolved by a conventional low molecular weight methyl cellulose with a weight average molecular weight of 10 to 20 kDa to improve safety and form a micelle to be soluble, thereby completing the present invention.

Therefore, an objective of the present invention is to provide a micelle particle for delivering a bioactive substance which includes methyl cellulose having a weight average molecular weight of 6 to 9.5 kDa.

Furthermore, another objective of the present invention is to provide a sustained release parenteral bioactive substance delivery composition by which the kidney toxicity problem can be resolved.

Furthermore, another objective of the present invention is to provide a bioactive substance carrier, in which a bioactive substance is carried in a micelle, comprising methyl cellulose having a weight average molecular weight of 6 to 9.5 kDa.

Furthermore, another objective of the present invention is to provide an external agent for skin, comprising methyl cellulose having a weight average molecular weight of 6 to 9.5 kDa and a bioactive substance.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below and can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

The terminology used herein is for the purpose of describing particular embodiments only and is not intended to be limiting the exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof and do not preclude the presence or addition of one or more other features, integers, steps, operations, elements, components and/or groups thereof.

With reference to the appended drawings, exemplary embodiments of the present invention will be described in detail below. To aid in understanding of the present invention, like numbers refer to like elements throughout the description of the figures, and the description of the same elements will not be iterated.

The terms used herein are defined as follows.

Figure 9:
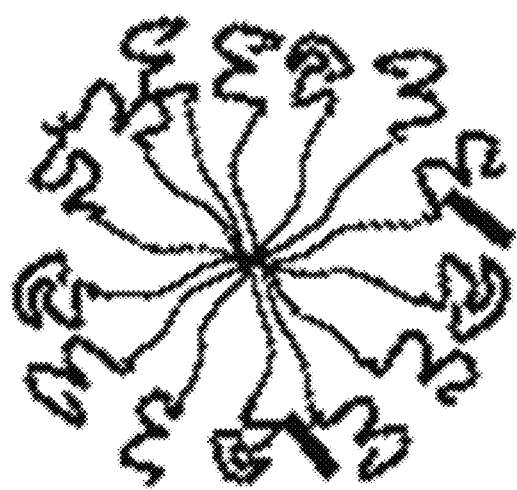
FIG. 9 shows a micelle formed in the present invention.
Figure 10A:
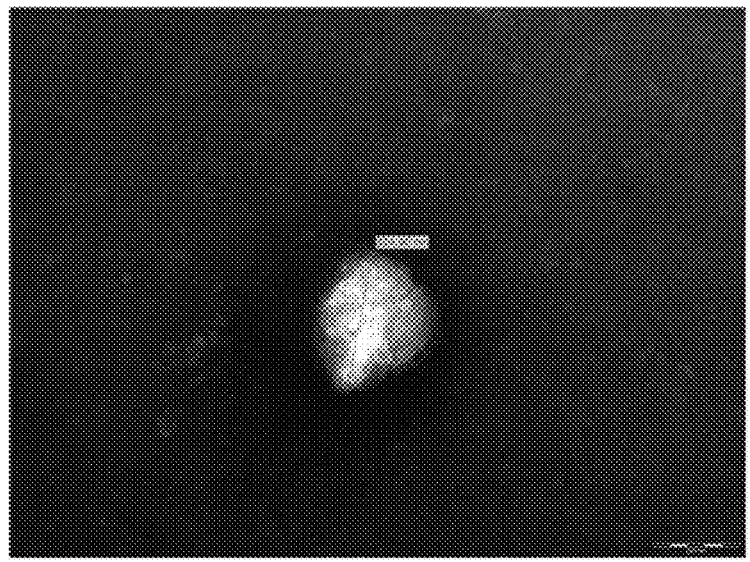
FIG. 10A shows transmission electron microscopy (TEM) results and DLS results of a case where a micelle is formed using the low molecular weight methyl cellulose of Preparation Example 1 without drug loading.
Figure 10A:
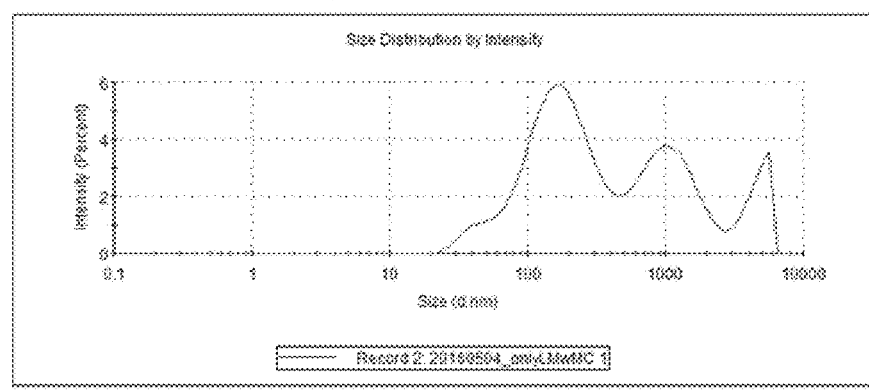
Figure 10B:
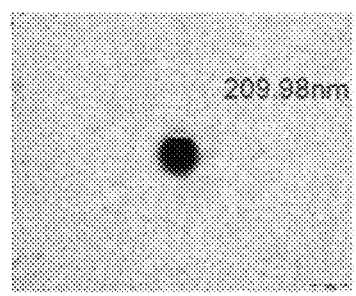
FIG. 10B shows TEM results and DLS results of a case where low molecular weight methyl cellulose micelles loaded with 1 mg of docetaxel (DTX) are formed.
Figure 10B:
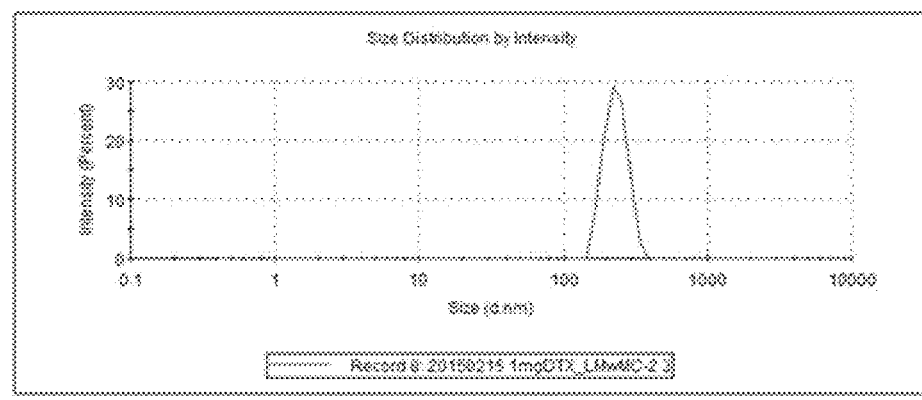

A "micelle" formed by a polymer is generally formed by self-assembly of an amphiphilic polymer in an aqueous solution and has a unique core-shell structure in which a poorly soluble drug may be loaded into the core. The amphiphilic polymer formed of hydrophilic residues with hydrophilicity and hydrophobic blocks with hydrophobicity to have both hydrophilic and hydrophobic properties is used therefor. When such an amphiphilic polymer is dispersed in an aqueous solution, it shows a tendency toward self-aggregation (i.e., self-assembly) to minimize contact with water and stabilize free energy by the hydrophobic interaction of hydrophobic blocks. A core is formed by the thus aggregated hydrophobic blocks and a shell is formed around the core by hydrophilic blocks to form a polymeric micelle having molecules physically bound to each other. The solubility of the polymeric micelle in an aqueous solution is increased by the hydrophilic blocks. The "micelle" in the present invention has a self-assembled form by methyl cellulose having a weight average molecular weight of 6 to 9.5 kDa, and as shown in FIG. 9, has a core-shell structure formed of a hydrophilic block of a hydroxyl group and a hydrophobic block of a methoxide group, and the average particle size thereof is 50 to 400 nm or 100 to 350 nm.

"Biodegradable" means that block copolymer components can chemically degrade within the body to form nontoxic components. A degradation rate is the same as or different from a release rate of a bioactive substance such as a drug.

"Biocompatible" means that a material interacts with the body without undesirable aftereffects.

"Sustained release" refers to the continual release of a bioactive substance such as a drug over a period of time.

"Controlled release" refers to control of the rate and/or quantity of a bioactive substance such as a drug delivered according to bioactive substance (ex, drug) delivery formulations of the present invention. The controlled release may be continuous or discontinuous, and/or linear or non-linear. This may be accomplished using one or more types of polymer compositions, loading of a bioactive substance such as a drug, inclusion of excipients or degradation enhancers, or other modifiers, administered alone, in combination or sequentially to produce the desired effect.

"Bioactive substance" refers to any compound or composition which, when administered to an organism (human or nonhuman animal), induces a desired pharmacologic, immunogenic, and/or physiologic effect by local and/or systemic action. Therefore, the term encompasses those compounds or chemicals traditionally regarded as drugs, vaccines, and biopharmaceuticals including molecules such as proteins, peptides, hormones, nucleic acids, gene constructs and the like. Further, it can be included as an active ingredient in cosmetics such as for whitening, antioxidation, moisturizing, UV blocking, conditioning, anti-inflammation, wrinkle improvement, elasticity enhancement or the like in addition to drugs.

"Drug" means any organic or inorganic compound or substance having bioactivity and used or adapted for therapeutic purposes. Poorly soluble drugs, hydrophilic drugs, low molecular weight drugs, high molecular weight drugs, proteins, oligonucleotides, DNA, and gene therapy agents are included in the broad definition of a drug.

"Peptide," "polypeptide," "oligopeptide," and "protein" may be used interchangeably when referring to a peptide or protein drugs and are not limited to particular molecular weights, peptide sequences or lengths, biological activity or therapeutic application areas.

"Therapeutic effect" means any improvement in the condition of a subject, human or animal treated according to the subject method, including obtaining a preventative or prophylactic effect, or any alleviation of the severity of signs and symptoms of a disease, disorder, or condition which may be detected by means of physical examination, laboratory or instrumental methods.

As used herein, unless otherwise defined in conjunction with specific diseases or disorders, the term "treat" or "treating" refers to: (i) preventing a disease, disorder or condition from occurring in an animal or human that may be predisposed to the disease, disorder and/or condition but has not yet been diagnosed as having it; (ii) inhibiting the disease, disorder or condition, that is, arresting its development; and/or (iii) relieving the disease, disorder or condition, that is, causing regression of the disease, disorder and/or condition.

The term "about or approximately" or "substantially" used in the present specification is intended to mean close to numerical values or ranges specified with an allowable error and intended to prevent accurate or absolute numerical values disclosed for understanding of the present disclosure from being illegally or unfairly used by any unscrupulous third party.

Hereinafter, the present invention is described in detail as follows.

The present invention relates to a drug delivery micelle nanoparticle which includes methyl cellulose having a weight average molecular weight of 6 to 9.5 kDa, and a sustained release parenteral drug delivery composition which includes methyl cellulose having a weight average molecular weight of 6 to 9.5 kDa.

The methyl cellulose is a polysaccharide based on a monomer such as represented by the following Formula 1, and the degree of substitution (degree of saturation, DS) of a methyl group thereof is 1.5 to 1.9, and the methyl cellulose has a viscosity of 15 cPs in a 2% methyl cellulose aqueous solution at 80° C. and has a weight average molecular weight of approximately 14,000 (60 kDa).

[Formula 1]

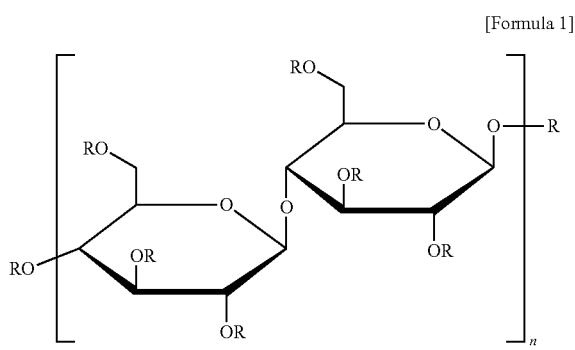

In the formula 1, R is hydrogen or methyl.

The methyl cellulose (MC) having a weight average molecular weight of 6 to 9.5 kDa according to the present invention has a degree of substitution of 1.5 to 1.9, and has a good dissolution property in an aqueous solution at a low temperature. The methoxide group which is the hydrophobic part of the methyl cellulose forms a core surrounding around a poorly soluble substance, and the hydrophilic part forms a surface in contact with water to form a micelle (FIG. 9) to be dissolved in water, and this is called solubilization.

The inventors of the present invention was able to resolve a kidney toxicity problem by formation of a micelle and excretion to outside the body by substantially reducing a weight average molecular weight of methyl cellulose to 6 to 9.5 kDa.

The low molecular weight methyl cellulose having a weight average molecular weight of 6 to 9.5 kDa of the present invention may be, for example, obtained by reducing a molecular weight by treatment with an enzyme, such as cellulase.

The methyl cellulose having a weight average molecular weight of 6 to 9.5 kDa of the present invention may be also referred to as a "low molecular weight methyl cellulose" or "LMwMC" in the present specification. Furthermore, the low molecular weight methyl cellulose of the present invention includes a methyl cellulose derivative within the range of forming micelles.

Particularly, a micelle particle including methyl cellulose having a weight average molecular weight of 6 to 9.5 kDa (LMwMC) of the present invention may load (or carry) a bioactive substance therein to be delivered into the body.

Here, the mixing ratio of LMwMC to a bioactive substance is preferably in a weight ratio of 10 to 25:1. When the amount of the bioactive substance is too small, there is a problem in that micelle nanoparticles carrying the bioactive substance are insufficiently formed and the bioactive substance may not be solubilized. When the amount of the bioactive substance is too much, there is a problem in that unnecessary methyl cellulose micelle nanoparticles containing no bioactive substance are increased, thereby increasing the toxicity of the substance or decreasing the efficiency of treatment.

A bioactive substance such as a drug (anticancer drug) is released from the micelle formed using the low molecular weight methyl cellulose of the present invention by active diffusion. Furthermore, the remaining drug is released after a certain period of time due to degradation of the micelle attributable to reduced stability. The micelles are delivered to cancer cells by the enhanced permeability and retention (EPR) effect in the body, thereby delivering the drug into cells.

As determined in Example 1, micelles formed of the low molecular weight methyl cellulose are gradually degraded in the body, converted into low molecular weight substances harmless to the human body, and excreted outside the body itself, and thus there is no need for a separate procedure such as a surgical operation to remove the micelles after release of the drug for a certain period. The release is mainly through the kidneys.

The low molecular weight methyl cellulose according to the present invention may be prepared into bioabsorbable, biodegradable, and biocompatible preparations.

The term "bioabsorbable" means that the polymer is capable of disappearing from its initial application site in the body, with or without degradation of the dispersed polymer molecules. Biodegradable means that the polymer can be broken or broken down in the body by hydrolysis or enymatic degradation.

The term "biocompatible" means that all of the components are nontoxic in the body.

The bioactive substance delivery composition of the present invention may be suitably injected or otherwise delivered (e.g., by implanting, placing into a body cavity or potential space, coating a tissue surface of the body or coating the surface of an implantable device) to humans or other mammals suffering from a disease state or condition against which the bioactive substance included in the bioactive substance delivery system is therapeutically effective. Particularly, the composition is preferably delivered parenterally.

The term "parenteral" includes intramuscular, intraperitoneal, intraabdominal, subcutaneous, intravenous or intraarterial.

The composition of the present invention may be typically formulated into an injectable preparation.

The low molecular weight methyl cellulose is required to have a low molecular weight to be easily excreted outside the body to be used as an injectable bioactive substance carrier. In the present invention, a low molecular weight which is one of the requirements of the micelle can be maintained by using low molecular weight methyl cellulose.

The injectable composition of the present invention may be injected or implanted into the body of a human or other mammal in any suitable manner, and preferably by injection through a hypodermic needle. For example, the composition of the present invention may be administered by injection or other means intraarticularly, intravascularly, into the urogenital tract, subcutaneously, intramuscularly, intradermally, intracranially, intrapericardially, intrapleurally, or into any body cavity or potential space. Alternately, the composition may be introduced via a catheter or a syringe to a joint such as during an arthroscopic procedure, or into the urogenital tract, into vasculature, into the pericardial or pleural cavity, or into any body cavity or potential space within the body, during operative, surgical, diagnostic or interventional procedures. In other applications, topical application of the composition to an open surgical or traumatic wound, to a burn, or to the skin or other tissue surface may be carried out.

Particularly, the composition of the present invention is a sustained release composition which slowly releases the drug in vivo when injected into a specific site in the body.

The composition of the present invention is suitable for use as a sustained or controlled release matrix for the bioactive substance. When the matrix is coupled with one or more bioactive substances contained homogeneously therein, a biodegradable sustained release bioactive substance delivery system is provided.

The term "sustained release" (i.e., extended release or controlled release) is used herein to refer to a bioactive substance delivery system or composition that is introduced into the body of a human or another mammal, or that is applied to an open wound, burn or tissue surface or into a body cavity or potential body space, and that continuously releases a stream of one or more bioactive substances over a predetermined time period and at a therapeutic level sufficient to achieve a desired therapeutic effect throughout the predetermined time period.

In a specific example of the present invention, it was determined that most of the loaded bioactive substance (drug) was able to be continuously released without an initial burst over a period of about 21 days to 25 days.

Furthermore, since the bioactive substance delivery composition of the present invention is degraded into harmless substances after a certain period of time and excreted outside the body through the kidneys as described above, when the composition according to the present invention is injected into a specific site in the body using a typical syringe or catheter, the bioactive substance (drug) is slowly released such that the bioactive substance (drug) is maintained at a constant concentration for a long time in the circulating blood, and thus expression of efficacy of the bioactive substance (drug) is excellent, and there is no need for a separate procedure such as a surgical operation to remove a bioactive substance carrier.

Therefore, a bioactive substance can be released to a target site of the subject in a controlled manner according to the sustained release bioactive substance carrier of the present invention.

In a specific example, site-specific release of a bioactive substance to a subject is provided using a micelle. In another specific example, a micelle includes one or more bioactive substances which can be administered to a subject such that the bioactive substance is released by diffusion from and/or degradation of the micelle.

Here, dosage values of the composition will vary with the type and severity of disease, disorder, or condition being treated. It is to be further understood that for any particular subject, specific dosage regimens should be adjusted over time according to the individual need and the professional judgment of the person administering or supervising the administration of the composition. In vivo dosages may be based on in vitro release studies in cell culture or on in vivo animal models.

As such, since the composition of the present invention releases a bioactive substance in a controlled manner, it provides optimal delivery of a bioactive substance. The result of controlled delivery is that the bioactive substance is delivered over a desired period of time. A slower and steadier rate of delivery may in turn result in a reduction in the frequency with which the bioactive substance should be administered to an animal.

Consequently, the low molecular weight methyl cellulose of the present invention has high biocompatibility and biodegradability, is suitable for a long term sustained release formulation, and increases the stability and effect of the bioactive substance, and thus is very usable as a bioactive substance carrier.

The composition according to the present invention may include low molecular weight methyl cellulose of the present invention at 0.01 to 90 wt % with respect to 100 wt % of the total composition. Specifically, it may be included at about 0.1 to 80 wt %, more specifically about 0.1 to 70 wt %, and further more specifically about 0.1 to 60 wt % with respect to the total composition. Furthermore, the amount of the composition to be administered may be 0.5 to 100 mg/kg/day one or several times, but can be suitably adjusted based on the severity of a disease, age, body weight, condition, sex, an administration route, a treatment period, etc.

Further, the composition according to the present invention may include a carrier which is acceptable for a bioactive substance, a drug, a cosmetic, or a health functional food in addition to the low molecular weight methyl cellulose.

Further, the micelle of the present invention may be effectively used as a sustained release bioactive substance carrier. Particularly, it is further effective in delivery of a poorly soluble drug.

The poorly soluble drug refers to a drug which is difficult to be solubilized due to low water solubility, also means a hydrophobic drug, and examples thereof include an anticancer drug or a drug for cardiovascular diseases such as arteriosclerosis, hyperlipemia and the like, but are not limited thereto, and may include any poorly soluble drug which is difficult to be solubilized. Specifically, examples of the poorly soluble drug include paclitaxel, docetaxel, tamoxin, anastrozole, carboplatin, topotecan, velotecan, imatinib, irinotecan, fluoxuridine, vinorelbine, gemcitabine, leuprolide, flutamide, zoledronate, methotrexate, camptothecin, cisplatin, vincristine, hydroxyurea, streptozocin, valrubicin, lovastatin, simvastatin, fluvastatin, atrovastatin, pitavastatin, pravastatin, rosuvastatin and the like, but are not limited thereto.

Examples of drug substances which may be included in the micelle of the present invention in addition to the poorly soluble drug include proteins, polypeptides, carbohydrates, inorganic substances, antibiotics, anti-neoplastic agents, local anesthetics, antiangiogenic agents, vasoactive agents, anticoagulants, immunomodulators, cytotoxic agents, antiviral agents, antibodies, neurotransmitters, psychotropic agents, oligonucleotides, lipids, cells, tissues, tissue or cell aggregates and combinations thereof. In addition, other drug substances include cancer chemotherapeutic agents, such as cytokines, chemokines, lymphokines, and substantially purified nucleic acids, and vaccines such as attenuated influenza virus. Substantially purified nucleic acids that can be incorporated include genomic nucleic acid sequences, cDNAs encoding proteins, expression vectors, antisense molecules that bind to complementary nucleic acid sequences to inhibit transcription or translation, and ribozymes. As such, there is basically no limitation on the types of usable drugs.

Furthermore, a variety of technologies by which a bioactive substance can be loaded (carried) into a micelle are known.

The bioactive substance is included at about 0.01 to 100 wt %, preferably about 1 to 95 wt %, and more preferably about 10 to 70 wt % in the micelle. The amount or concentration of the bioactive substance included in the micelle will vary with the absorption, inactivation, and excretion rates of the bioactive substance.

In an example, the micelle of the present invention prepared using the above-described method is administered into the body through intravenous injection, circulates in the bloodstream and is delivered to a target site with tumors through a property in which cells forming cancer tissue become loose by the enhanced permeability and retention (EPR) effect. The bioactive substance (drug) contained in the micelle may be actively diffused, or may be released to the target site in a controlled manner by degradation of the micelle over time.

Further, the present invention includes a bioactive substance carrier in which a bioactive substance is loaded (carried) into a micelle including methyl cellulose having a weight average molecular weight of 6 to 9.5 kDa.

All the above described content related to the micelle particle and the bioactive substance delivery composition is directly applicable to the bioactive substance carrier.

Here, the present invention includes a method of treating a disease, disorder, or condition including introduction of the bioactive substance into a required subject (patient), and the method of preparing the delivery system of the present invention.

That is, the present invention may include a sustained release pharmaceutical composition for releasing a bioactive substance which includes a micelle including methyl cellulose having a weight average molecular weight of 6 to 9.5 kDa and a target bioactive substance.

Furthermore, the present invention may include an external agent for skin which includes methyl cellulose having a weight average molecular weight of 6 to 9.5 kDa and a bioactive substance.

All the above described content related to the micelle particle and the bioactive substance delivery composition in the above is directly applicable to the external agent for skin.

In the present specification, the "external agent for skin" is a concept that covers the whole composition applied to the skin, and for example, is a concept including various cosmetics such as a basic cosmetic, a makeup cosmetic, a hair care cosmetic or the like; drugs and quasi-drugs such as an ointment, a cream, a lotion, a gel, a patch, etc.

The content of the low molecular weight methyl cellulose of the present invention used in the agent for external use is not particularly limited as long as it can secure a desired delivery capability for a bioactive substance, and may be suitably determined by those skilled in the art depending on the desired degree. For example, the content may be 0.01 to 90 wt % with respect to 100 wt % of the total composition. Specifically, the content may be about 0.1 to 80 wt %, more specifically about 0.1 to 70 wt %, and further more specifically about 0.1 to 60 wt % with respect to the total composition. The cosmetic may be any formulation known as a cosmetic, and for example, may be one formulation selected from the group consisting of a skin, an emulsion, a cream, a sun cream, a foundation, an essence, a gel, a pack, a mask pack, a foam cleanser, a body cleanser, a softener, an eyeliner, a shampoo, a rinse, a soap, a hair conditioner, a hair tonic, a hair cream, a hair styling gel, a lubricant, a toothpaste and a wet tissue, but is not limited thereto.

Hereinafter, the present invention will be described in detail through examples. The following examples are merely provided to illustrate the present invention, and the scope of the present invention is not limited to the following examples. The examples are provided to complete the disclosure of the present invention and to fully disclose the scope of the present invention to those of ordinary skill in the art, and the present invention is only defined by the range of the appended claims.

EXAMPLES

Preparation Example: Preparation of Low Molecular Weight Methyl Cellulose Having Weight Average Molecular Weight of 8.5 kDa 8 g of methyl cellulose (molecular weight: 60 kDa; manufactured by Sigma-Aldrich Co. LLC.] was added to 200 ml of tertiary distilled water to prepare a 4% solution in total. The methyl cellulose aqueous solution was stirred under conditions of 80° C. and 210 rpm for 30 minutes to increase the degree of dispersion. The methyl cellulose aqueous solution was stirred in a low temperature room (4° C.) for 1 hour to further increase the solubility of the methyl cellulose in water. Next, the methyl cellulose aqueous solution was stirred under conditions of room temperature (24 to 25° C.) and 210 rpm for 30 minutes.

The target unit of the methyl cellulose is 30 units/ml, and 51.75 mg of endo-cellulase (Worthington Biochemical Corp.) with an enzyme effect of 105 units/mg was added to the methyl cellulose aqueous solution. The methyl cellulose aqueous solution was stored and stirred under conditions of room temperature (24 to 25° C.) and 210 rpm for 3 days. Since the function of the cellulase enzyme is to cut from the inside of the polysaccharide chain in the case of endo-cellulase, the activity of the cellulase is not maintained after 3 days. Therefore, the temperature of the stirrer was raised to 80° C. and stirred for 10 to 15 minutes to inactivate the cellulase in the methyl cellulose aqueous solution on day 3. Since an increase in the temperature results in decreased solubility of the methyl cellulose in water, the mixture was further stirred in a low temperature room (4° C.) for 1 hour to increase the solubility of the methyl cellulose. Subsequently, the methyl cellulose aqueous solution was filtered using a 0.22 μm polyvinylidene fluoride (PVDF) filter to primarily filter large polymers. The filtered methyl cellulose aqueous solution was added to a dialysis membrane (Spectrum Lab., Filtration limit: 6 to 9.5 kDa) and dialyzed in the tertiary distilled water in the low temperature room (4° C.) for 2 days. After 2 days, the dialysis membrane was removed and the tertiary distilled water outside the dialysis membrane was collected and stored in a freezer at −70° C. for 1 day (since low molecular weight methyl cellulose was required, the solution outside the dialysis membrane was collected). Only moisture in the frozen solution was evaporated under conditions of −76° C. and 20 to 24 mTorr in a freeze-dryer for 5 to 7 days. Then, only low molecular weight methyl cellulose powder with an average molecular weight of 8.5 kDa was collected after lyophilization.

Example 1: Preparation of Low Molecular Weight Methyl Cellulose Micelle Having Weight Average Molecular Weight of 8.5 kDa and Analysis of Characteristics Thereof Micelles were prepared using only the low molecular weight methyl cellulose obtained above, and characteristics thereof were analyzed.

The micelles were prepared using a thin-film hydration method.

First, 1 ml of hexafluoro-2-propanol (HFP) was dissolved in each vial containing 1 mg of docetaxel (DTX) and 20 mg of low molecular weight methyl cellulose (LMwMC) with an average molecular weight of 8.5 kDa, and the two solutions were mixed in a rotary evaporator. The mixture was slowly rotated at 36° C. until HFP evaporated to form a thin film. After 3 ml of tertiary distilled water was added thereto, the degree of dispersion was increased by slowly rotating the mixture at 50° C. for 10 minutes to make the formed thin-film into an aqueous solution. Finally, the mixture was slowly rotated for 30 minutes at a temperature of −4° C. to increase solubility, and thereby an aqueous solution containing a low molecular weight methyl cellulose micelle loaded with an anticancer agent was completed.

(1) Measurement of Critical Micelle Concentration (CMC)

5 μg of 1,6-diphenyl-1,3,5-hexatriene (DPH, Mw=232.32) was dissolved in HFP to prepare a 0.86 mM stock solution, and 2.5 mg of low molecular weight methyl cellulose was dissolved in 1 ml of HFP and serially diluted until 2.4 μg to prepare 2.5 mg/ml to 2.4 μg/ml samples. Each low molecular weight methyl cellulose sample was introduced into a glass beaker, a 5 uM stock solution was added thereto, and the mixture was conjugated using a thin-film hydration method. First, the mixed two solutions were evaporated using an evaporator, 3 ml of secondary distilled water was added thereto, and the mixture was rotated at 47° C. for 10 minutes to increase the degree of dispersion. Thereafter, the mixture was added to ice and rotated for 30 minutes to increase solubility, and each completed sample was placed on a 96-well DC plate and the light absorbance thereof was measured with a UV/Vis fluorescence spectrophotometer (Infinite M200Pro, TECAN, Switzerland) with excitation at 355 nm and emission at 428 nm to determine at which concentration micelles are formed well.

Figure 1:
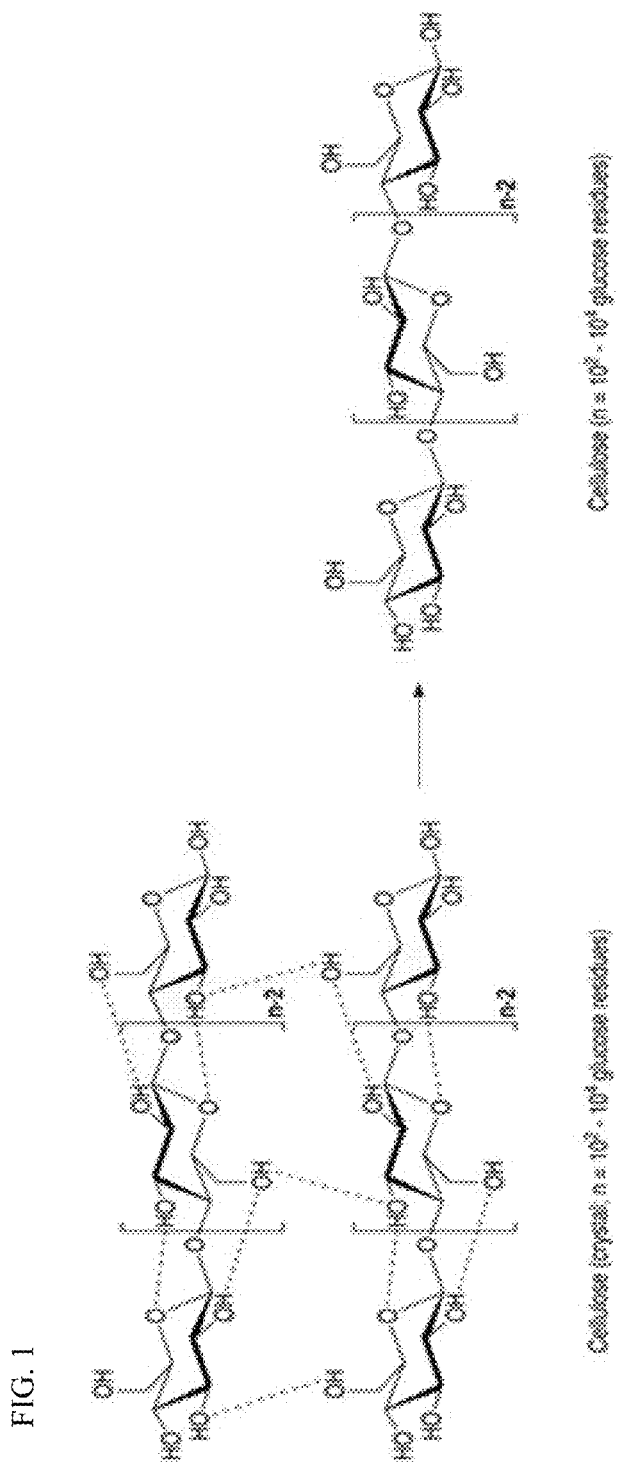
FIG. 1 shows a principle of endo-cellulase among cellulase enzymes of cutting from the inner chain of a polysaccharide.
Figure 2:
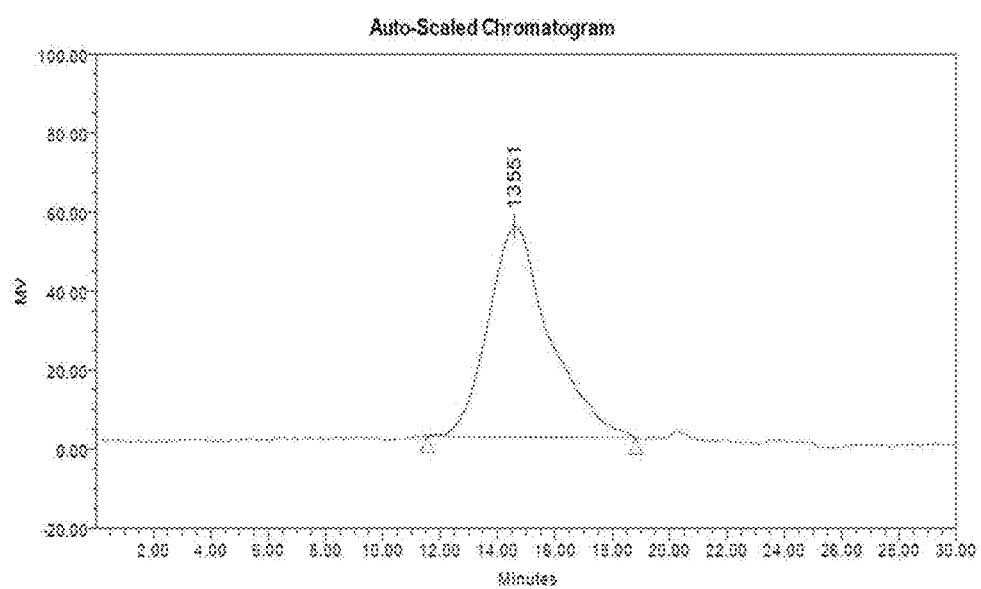
FIG. 2 shows a result of measuring methyl cellulose with a molecular weight of 60 kDa used in a preparation example before the process of being prepared into a low molecular weight polysaccharide using gel permeation chromatography (GPC)
Figure 3:
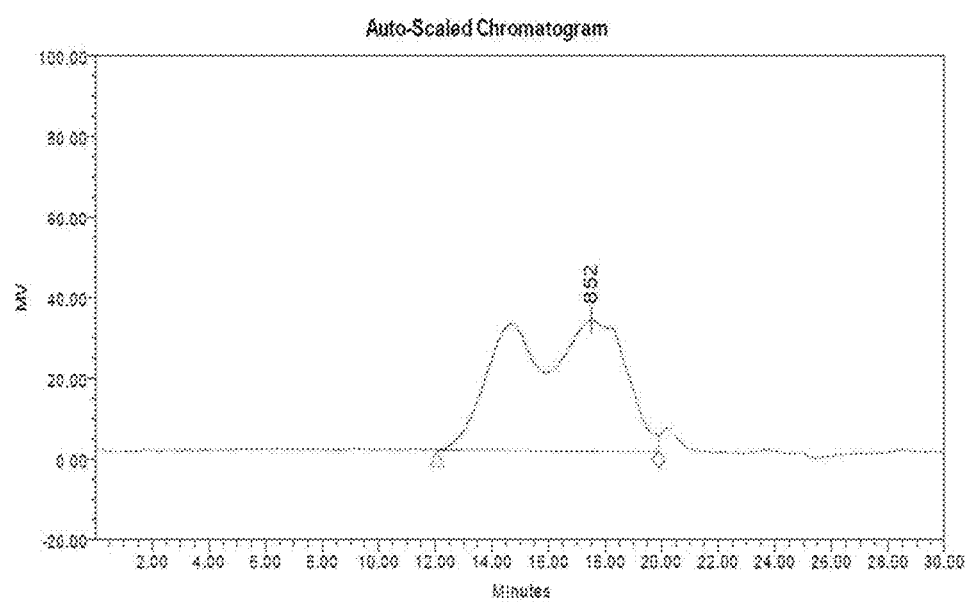
FIG. 3 is a result of measuring a 4% methyl cellulose aqueous solution using GPC after treatment with a cellulase enzyme and reaction for 3 days, showing that a molecular weight is about 9,000 (15 kDa)
Figure 4:
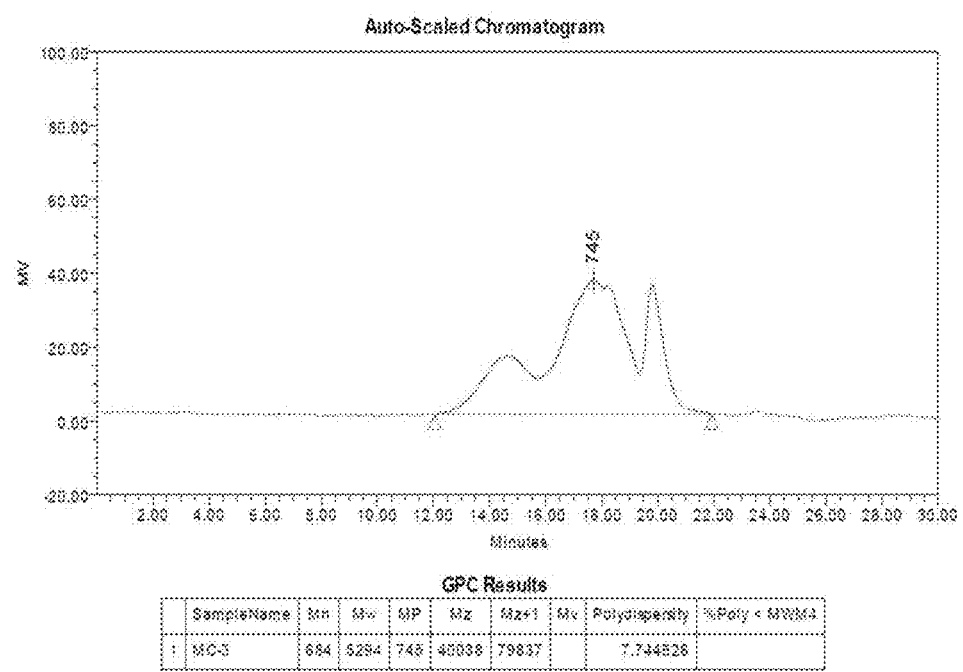
FIG. 4 is a result of measuring a methyl cellulose aqueous solution using GPC after freeze-drying the methyl cellulose aqueous solution filtered through a dialysis membrane (Spectrum Lab., filtration limit: 6 to 8 kDa) after treatment with a cellulase enzyme, showing that a molecular weight is about 5,294 (8.5 kDa)
Figure 5:
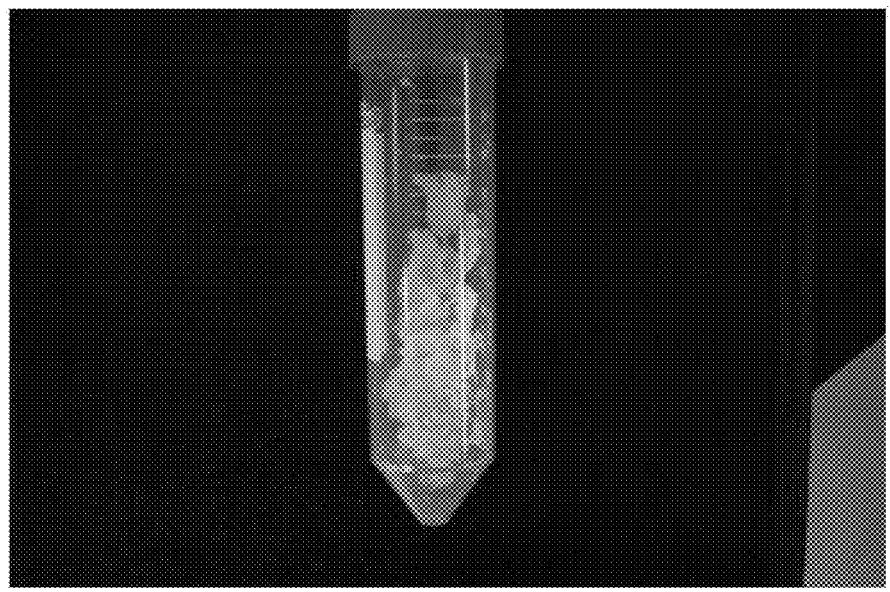
FIG. 5 shows methyl cellulose in powder (solid) form with an average molecular weight of 8.5 kDa which is finally obtained in a preparation example.
Figure 6:
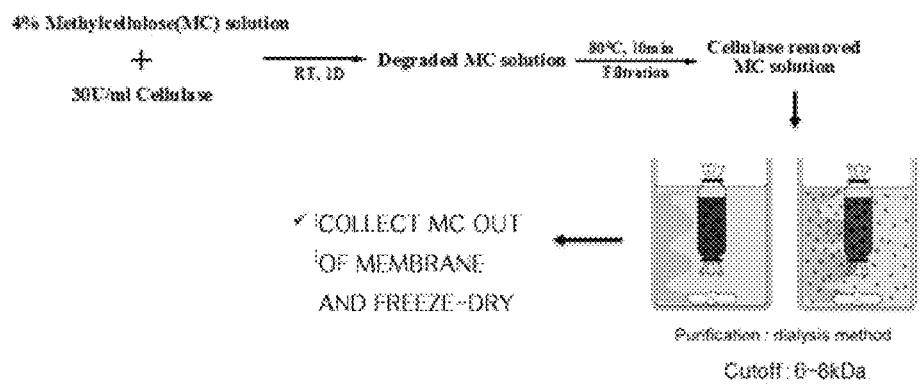
FIG. 6 is a schematic view showing a process of preparing low molecular weight methyl cellulose according to Preparation Example 1.
Figure 7:
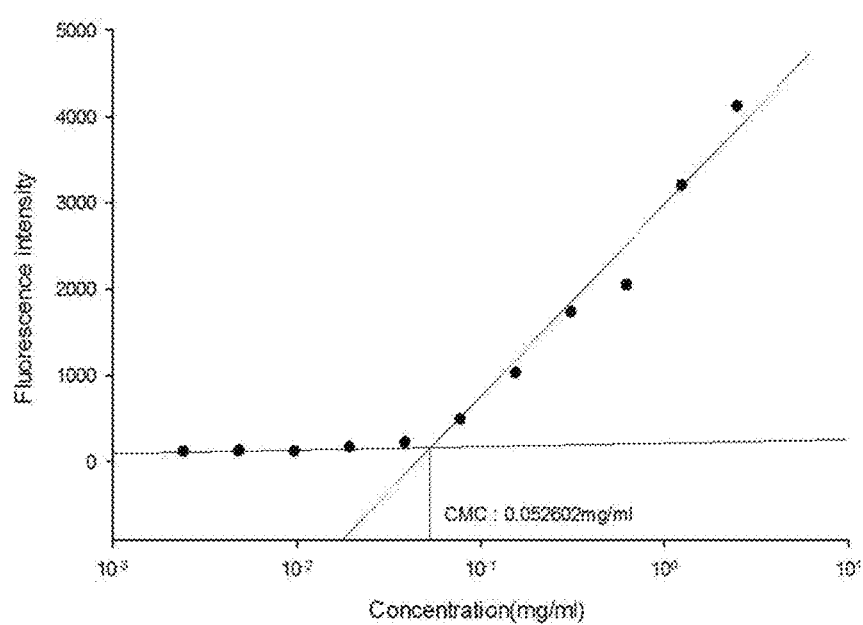
FIG. 7 shows a result of measuring a critical micelle concentration (CMC) of the low molecular weight methyl cellulose of Preparation Example 1.

As shown in FIG. 7, it was determined that low molecular weight methyl cellulose micelles with an average molecular weight of 8.5 kDa were formed from a concentration of 0.0526 mg/ml or more (2) Cytotoxicity Analysis A total of 500 μl of a complete medium was laid on a 24-well plate by calculation such that $2 \times 10^4$ cells of a B16F10 mouse melanoma cell line obtained from a Korean cell line bank was contained in each well of a 24-well plate (seeding). Cells were grown in an environment of 5% $CO_2$ and 37° C. for 24 hours. For statistical significance, the number of wells in each group was 4, each well was treated with 50 μl of an untreated control group and 50 μl of treated groups (62.5, 125, 250, 500 and 1,000 μg/1 ml of PBS) treated with low molecular weight methyl cellulose at different concentrations, and then incubated again in an environment of 5% $CO_2$ and 37° C. for 24 hours (treating). After 24 hours, the solution contained in each well was all removed, and 500 μl of a complete medium in which MTT (3[4,5-dimethylthiazol-2-yl]-2,5-diphenyltetrazolium bromide) and a medium were mixed at a ratio of 1 ml:9 ml were added per well and the mixture was incubated in an environment of 5% $CO_2$ and 37° C. for 2 hours. After 2 hours, each complete medium contained in each well was taken out, 500 μl of dimethyl sulfoxide (DMSO) was added per well, the mixture was incubated at 37° C. for 15 minutes and shook for 5 seconds, and then the light absorbance thereof was measured at a wavelength of 570 nm using a UV spectrophotometer.

Figure 8:
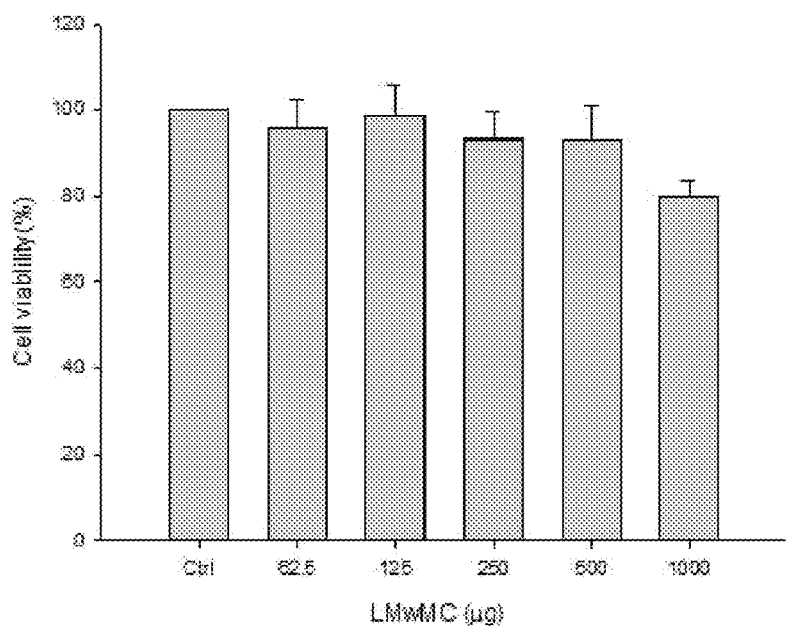
FIG. 8 shows cytotoxicity according to a concentration of the low molecular weight methyl cellulose of Preparation Example 1.

The results of the cytotoxicity test are shown in FIG. 8. It was determined that the low molecular weight methyl cellulose micelle of the present invention does not affect cell viability.

(3) Determination of Micelle Size

Methyl cellulose micelles were prepared by dissolving 10 mg of the prepared low molecular weight methyl cellulose in 1 ml of distilled water.

The low molecular weight methyl cellulose micelles containing 1 mg of docetaxel were prepared in the same manner as the method of preparing micelles using a thin-film hydration method, and each micelle was prepared using the same method while varying the added amounts of docetaxel and methyl cellulose. That is, 1 mg of docetaxel and 20 mg of low-molecular-weight methyl cellulose were used in the case of 1 mg-containing micelles.

The morphology of each micelle thus prepared was confirmed by transmission electron microscopy.

In order to measure DLS, 1 ml of tertiary distilled water was added to powder prepared by freezing each micelle prepared by the above-described method for 1 day and freeze-drying the micelle for about 3 to 5 days to prepare samples, and the size thereof was measured using a machine. As a result, it can be seen that the case of micelles containing docetaxel were formed more compactly as compared with the case of micelles containing no docetaxel as shown in FIG. 10. Although the amounts of docetaxel contained in low molecular weight methyl cellulose are different, it can be observed that micelles having a polydispersity (PDI) of 0.2 or less and the similar size of nearly 200 nm are formed in the aqueous solution.

As shown in FIG. 10, it was determined by transmission electron microscopy (TEM) that a spherical micelle was formed of DTX and low molecular weight methyl cellulose, and the sizes of low molecular weight methyl cellulose in which DTX was not loaded and a micelle loaded with 1 mg of DTX were 324.9 nm and 209.98 nm, respectively. Further, results similar to those of TEM were determined by dynamic light scatter (DLS) measurement.

Example 2: Measurement of Drug Loading Rate of Low Molecular Weight Methyl Cellulose Micelle An acetonitrile (ACN) based DTX standard graph was made using a Breeze program (Version 3.30, Waters, Milford, Mass.) to measure a drug loading rate and drug content by HPLC (C18 HPLC column was used).

8 samples were prepared by serial dilution of 500 µg of DTX/1 ml of ACN and a linear equation standard graph was formed (the R-squared value of the standard curve represents reliability and is 0.99 or more, and thus this graph is a reliable reference graph).

A low molecular weight methyl cellulose micelle aqueous solution with 1 mg of docetaxel prepared by the above-described method of preparing micelles was frozen for 1 day and formed into a powder form by lyophilization for about 3 to 5 days. 1 ml of ACN was added to this powder, the mixture was centrifuged at 13,000 rpm for 3 minutes, a supernatant (DTX+ACN) separated from the low molecular weight methyl cellulose was extracted and introduced into a HPLC column after filtering. Using the sample, the drug loading rate and content were measured by the HPLC machine and Breeze program (Version 3.30, Waters, Milford, Mass.). The amount of the drug in the solubilized aqueous solution measured by HPLC was substituted into the following Equations 1 and 2 to calculate the drug loading rate and content.

The drug loading rate and drug content of the micelle of Example 1 each were measured by the following Equations 1 and 2, and results are as shown in the following Table 1.

Drug loading rate (%)=Total amount of drug in solubilized aqueous solution/Amount of initially injected drug×100     [Equation 1]

Drug content (%)=Total amount of drug in solubilized aqueous solution/Weight of solubilized aqueous solution×100     [Equation 2]

(The initially injected drug, strictly speaking, is low molecular weight methyl cellulose containing docetaxel, and a micelle is formed by DTX and LMwMC at a weight ratio of 1:20. Therefore, it is preferable that the detected amount of DTX is about 4 to 5% of the amount of the initially injected drug as a result of quantifying the drug content by HPLC.)

TABLE 11

| Classification (n = 3) | Amount of initially injected low molecular weight methyl cellulose containing docetaxel (µg) | Drug loading rate (loading efficiency) | Drug content (loading contents) |
| --- | --- | --- | --- |
| Value | 1,000 | 71.6 ± 15.0% | 4.47 ± 0.67% |

Figure 11:
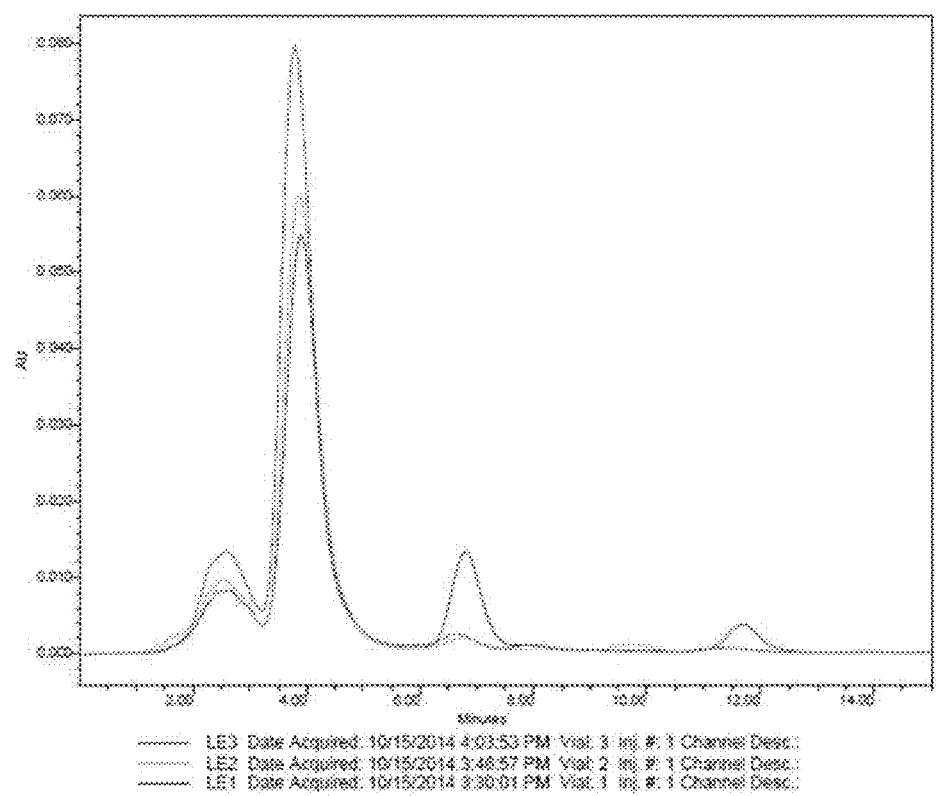
FIG. 11 shows HPLC analysis results for determining the retention time of DTX.
Figure 12:
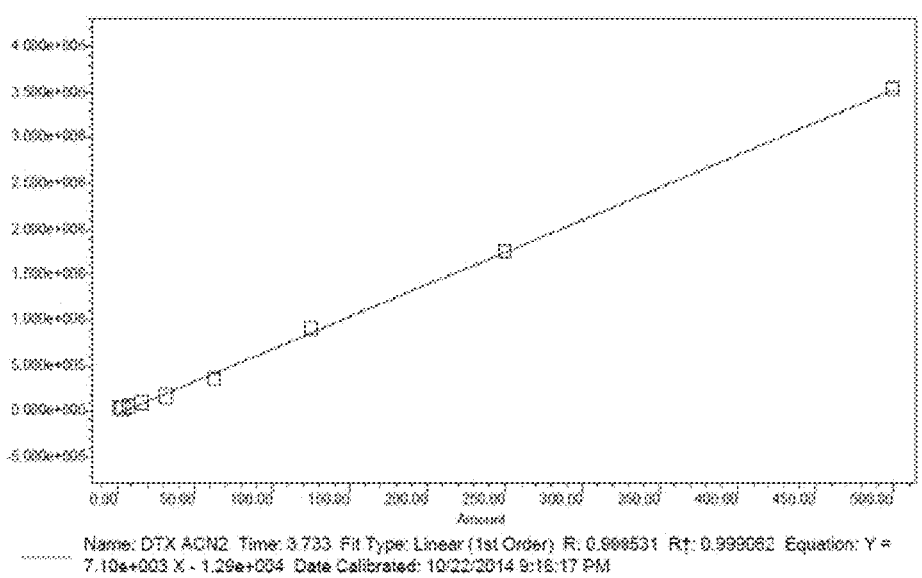
FIG. 12 shows HPLC analysis results of low molecular weight methyl cellulose micelles containing DTX at a concentration ranging from 3.9 to 500 µg/ml.

FIG. 11 shows an experiment performed to determine DTX detection peaks at how many seconds, that is, to determine the retention time of DTX by HPLC analysis using three low molecular weight methyl cellulose micelle samples loaded with 1 mg of DTX. It can be seen from the experiment result that peaks shown at 3.73 seconds are peaks indicating the detection of DTX. It can be seen from the result of HPLC analysis of FIG. 11 that peaks shown at 3.73 seconds in the graph indicate the light absorbance value of DTX FIG. 12 shows analysis performed on low molecular weight methyl cellulose micelles containing DTX at different concentrations of 3.9 to 500 µg/ml using an HPLC machine as in FIG. 11. Here, a result similar to that of the graph of FIG. 11 is obtained while the vertical axis (light absorbance) will vary by concentration (the higher the amount of DTX, a higher light absorbance is measured).

Since it was found through FIG. 11 that peaks detected at 3.73 seconds are peaks indicating an amount of DTX, a standard with respect to light absorbance at each DTX concentration was established by converting a light absorbance value detected at 3.73 seconds into a linear equation graph. That is, a graph of FIG. 12 is used as a standard graph for determining the amount of DTX when the release rate of docetaxel is measured in FIG. 13

Example 3: Drug Release Efficacy of Low Molecular Weight Methyl Cellulose Micelle (In Vitro Release Test)

A drug release test was conducted to determine the ability of the micelle of Example 1 to release drugs.

A solution prepared by dissolving the low molecular weight methyl cellulose powder with docetaxel obtained by freeze-drying the micelle prepared above in a PBS buffer was introduced into a dialysis membrane (MWCO: 3,500 Da) and the top and bottom of the membrane were tightly sealed with a string. The dialysis membrane was incubated with shaking at 37° C. and 100 rpm in a release medium (saline buffer (pH 7.4) containing 5% ACN). Since DTX has a strong dissolution property in ACN, it would migrate out of the dialysis membrane and be dissolved in the release medium. Therefore, a new release medium was replaced at each set time interval, and the obtained release medium was quantitated by the HPLC machine to determine how much drug was contained.

Figure 13:
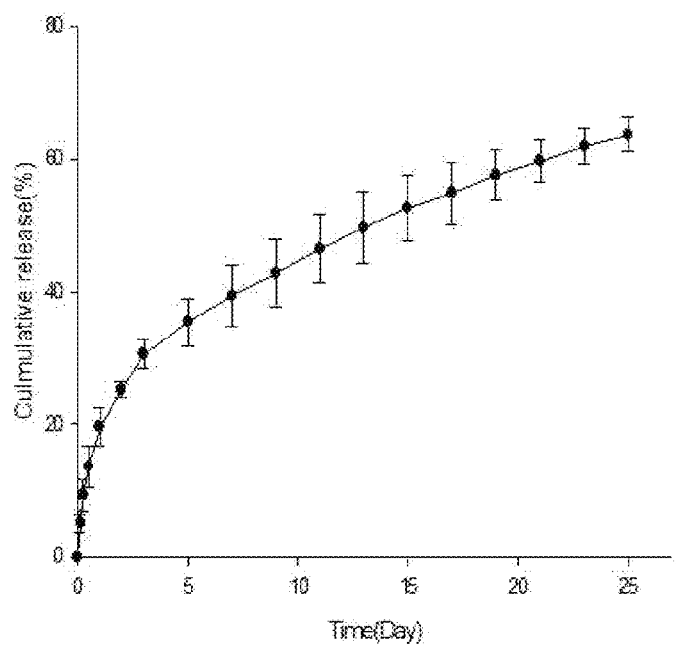
FIG. 13 shows a drug release rate of a formulation (micelle of Example 1) in which docetaxel is loaded into low molecular weight methyl cellulose of the present invention.

As a result, it was confirmed that about 60% of the drug was slowly released from the micelle for 25 days as shown in FIG. 13.

Example 4: Determination of In Vitro Drug Efficacy of Low Molecular Weight Methyl Cellulose Micelle A total of 500 µl of a complete medium was laid on a 24-well plate by calculation such that $2 \times 10^4$ cells of a B16F10 mouse melanoma cell line obtained from a Korean cell line bank was contained in each well of a 24-well plate (seeding). Cells were grown in an environment of 5% $CO_2$ and 37° C. for 24 hours. In addition to an untreated control group and a group only treated with PBS, 5,10,25,50,100 and 250 µg of micelles with 1 mg of an anticancer drug (DTX) prepared using low molecular weight methyl cellulose were each dissolved in 50 µl of PBS, and 50 µl thereof was placed in each well, and incubated in an environment of 5% $CO_2$ and 37° C. for 24 hours (treating). For statistical significance, the number of wells in each group was 4. After 24 hours, a medium containing the drug in each well was removed, and 500 µl of a complete medium in which MTT (3-[4,5-dimethylthiazol-2-yl]-2,5-diphenyltetrazolium bromide) and a medium were mixed at a ratio of 1 ml:9 ml were added per well and the mixture was incubated in an environment of 5% $CO_2$ and 37° C. for 2 hours. After 2 hours, 500 µl of the complete medium contained in each well was removed, 500 µl of DMSO was added thereto, the mixture was incubated at 37° C. for 15 minutes and shook for 5 seconds, and then the light absorbance thereof was measured at a wavelength of 570 nm using a UV spectrophotometer to determine cell viability.

Figure 14:
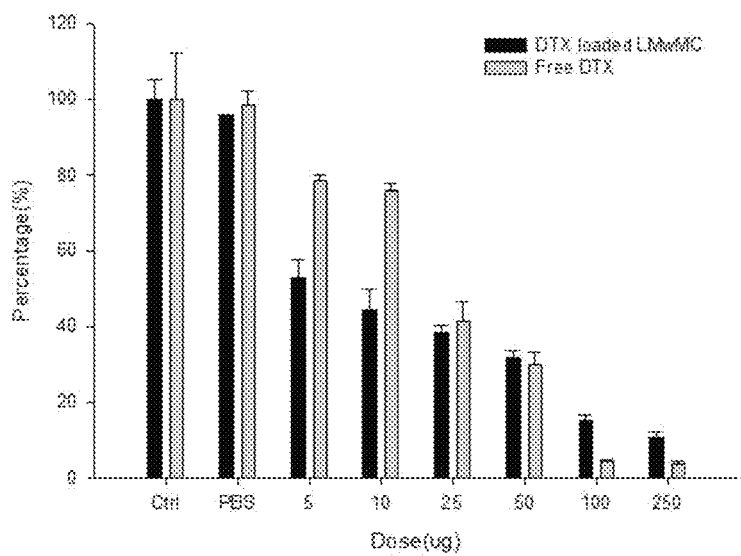
FIG. 14 shows light absorbance (cell viability) at a wavelength of 570 nm of a case of treatment with docetaxel only and a case of treatment with a formulation (micelle of Example 1) where docetaxel is loaded into the low molecular weight methyl cellulose of the present invention.

FIG. 14 is a graph of the cell viability measured by MTT assay, indicating how many B16F10 cells died depending on the amount of drug applied thereto relative to the number of living cells in a control group defined as 100%. A DTX-loaded LMwMC resulted in better anti-cancer effects by killing cancer cells more effectively as compared with the case of free DTX (particularly, the difference in treatment effect was significant when 5 μg of the drug was used, and thus it can be seen that the difference in treatment effect is significant even when a small amount of drug is injected.)

The MTT solution forms formazan crystals, which are purple-colored, only in the mitochondria of living cells. When the crystals are dissolved using DMSO to be converted into a liquid form because the crystals are insoluble, and are irradiated with light at a wavelength of 570 nm, the stronger the purple color is (the more formazan crystals formed due to a larger number of living cells, the stronger the purple color), a higher absorbance is measured.

As shown in FIG. 14, the formulation in which the anticancer agent is loaded into the low molecular weight methyl cellulose micelle exhibited a similar or excellent effect as compared with the case of treatment with only the anticancer drug.

Example 5: Determination of In Vivo Drug Efficacy of Low Molecular Weight Methyl Cellulose Micelle (Intratumoral Injection)

This experiment is a preliminary experiment prior to intravenous injection, and is an experiment for determining how much of an anticancer effect is exhibited by the drug in the tumor when the drug is delivered directly to the cancer site.

(1) Preparation of Tumor Animal Model

B16F10 melanoma cells grown in an environment of 5% $CO_2$ and 37° C. were injected into 6-week-old male C57BL/6 mice.

First, after the mice were anesthetized with 50 μl of an anesthetic prepared by mixing 100 mg/kg of ketamine with 10 mg/kg of xylazine, B16F10 melanoma cells were injected subcutaneously in the left rear flank of the mice to prepare tumor animals. When the volume of the tumor reached ~100 mm³, the tumor animals were divided into 6 groups.

(2) Determination of Tumor Size

The day when the tumor animals were divided into 6 groups when a tumor volume reached ~100 mm³ after preparation of the tumor animal models was defined as day 0. 50 μl of PBS was injected intratumorally into mice of a control group and 50 μl of PBS having 2 mg of low molecular weight methyl cellulose containing no drug were injected intratumorally into mice of an LMwMC group, and in the case of other groups treated with drugs, low molecular weight methyl cellulose powder with 1 mg of DTX obtained after lyophilization was dissolved in PBS depending on the concentration of each group and 50 μl of the mixture was injected intratumorally into each mouse on day 0. (mice were injected with 50 μl of PBS on day 0 in the case of the control group. 2 mg of LMwMC containing no drug was dissolved in 50 μl of PBS and the mixture was injected intratumorally into mice of the LMwMC group. 50 μl of an intravenous formulation prepared at a ratio of 3.125% of Tween 80, 3.125% of ethanol and 96.75% of PBS and containing 0.1 mg of docetaxel was injected intratumorally into mice of a Taxotere (5 mg/kg) group. The prepared 1 mg-DTX loaded LMwMC powder was dissolved in 500 μl of PBS and 50 μl of the mixture was injected intratumorally per mouse in a DTX-loaded LMwMC (5 mg/kg) group. The prepared 1 mg-DTX loaded LMwMC powder was dissolved in 250 μl of PBS and 50 μl of the mixture was injected intratumorally per mouse in a DTX-loaded LMwMC (10 mg/kg) group. The prepared two 1 mg-DTX loaded LMwMC samples each were dissolved in 125 μl of PBS to prepare a total of 250 μl of a sample, and 50 μl of the sample was injected intratumorally per mouse in a DTX loaded LMwMC (20 mg/kg) group.) After the mice were then fixed by grabbing the tails thereof at 2-day intervals for a total of 14 days, the size of the tumor in the left posterior flank was measured using a vernier caliper. The size of the tumor in the mouse was measured using a major axis of the vernier caliper with a graduation of 1 mm. After the long axis and short axis of the tumor were measured, the volume of the tumor was measured by the following Equation 3.

$$\text{Volume of tumor (mm}^3\text{)} = \frac{1}{2}ab^2 \qquad \text{[Equation 3]}$$

(a: long axis, b: short axis)

Figure 15:
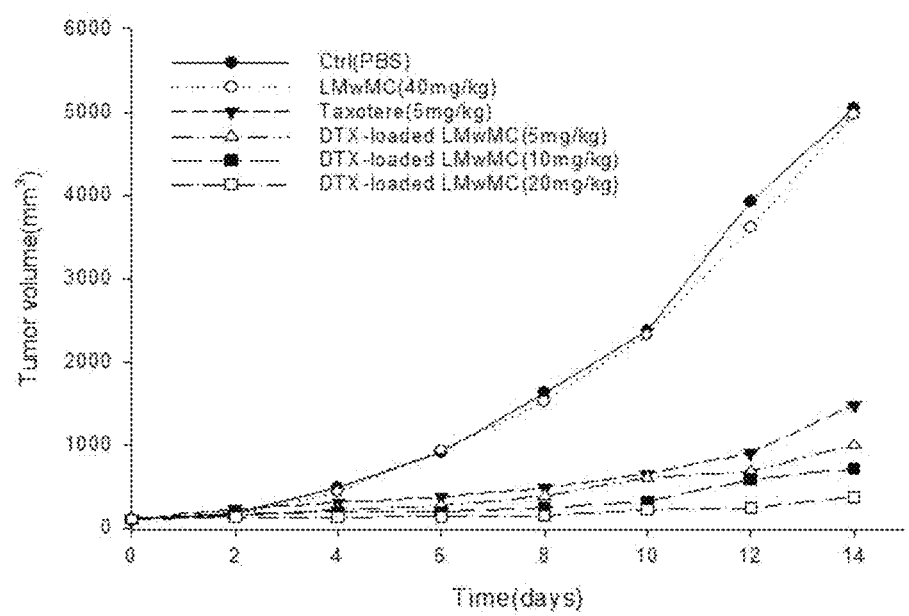
FIG. 15 is a graph showing a tumor size of a tumor animal model prepared by allografting B16F10 melanoma tumor cells into the right femoral subcutis of C57BL/6 mice after local injection (intratumoral injection) of a control group and a treatment group into tumors.

The data of FIG. 15 indicates the average value of tumor sizes of 5 animals for each group.

Figure 16:
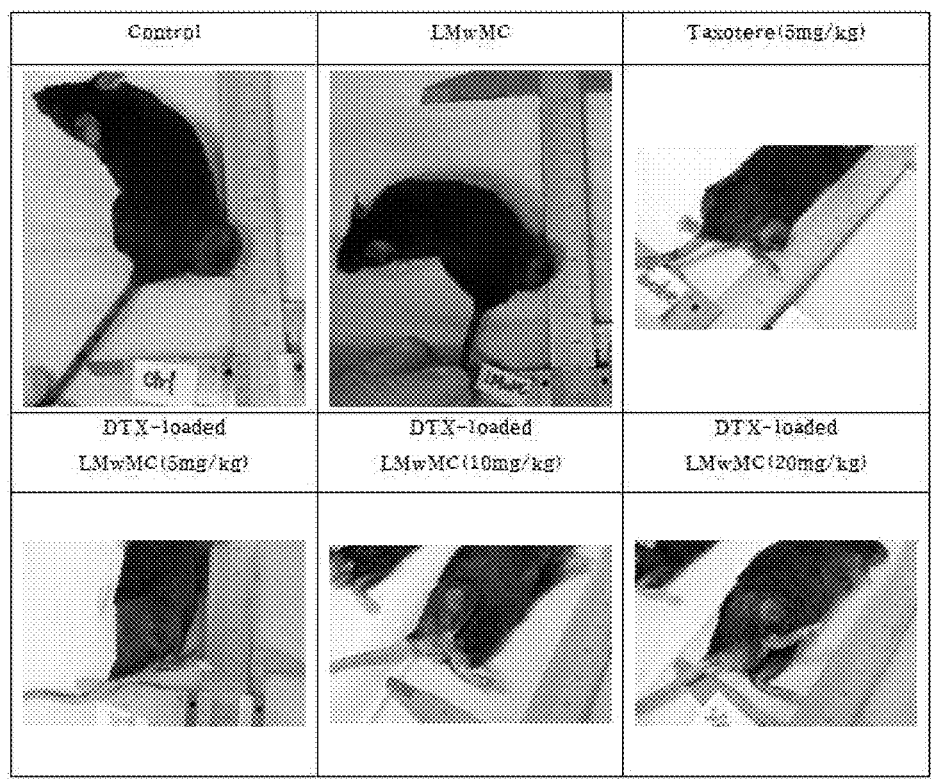
FIG. 16 is a picture of mice for determining a tumor size at day 14 after local injection (intratumoral injection) of a control group and a treatment group (micelle of Example 1) into tumors of tumor animal models.

As a result, as shown in FIGS. 15 and 16, a formulation in which an anticancer drug is loaded in a low molecular weight methyl cellulose micelle was determined to show an excellent anti-cancer effect as compared with a control group and even when compared with Taxotere which is an existing DTX medicine.

(3) Determination of Change in Weight

After intratumoral injection on day 0, each mouse was placed on an electronic scale at 2-day intervals for a total of 14 days, and the measured value was observed.

Figure 17:
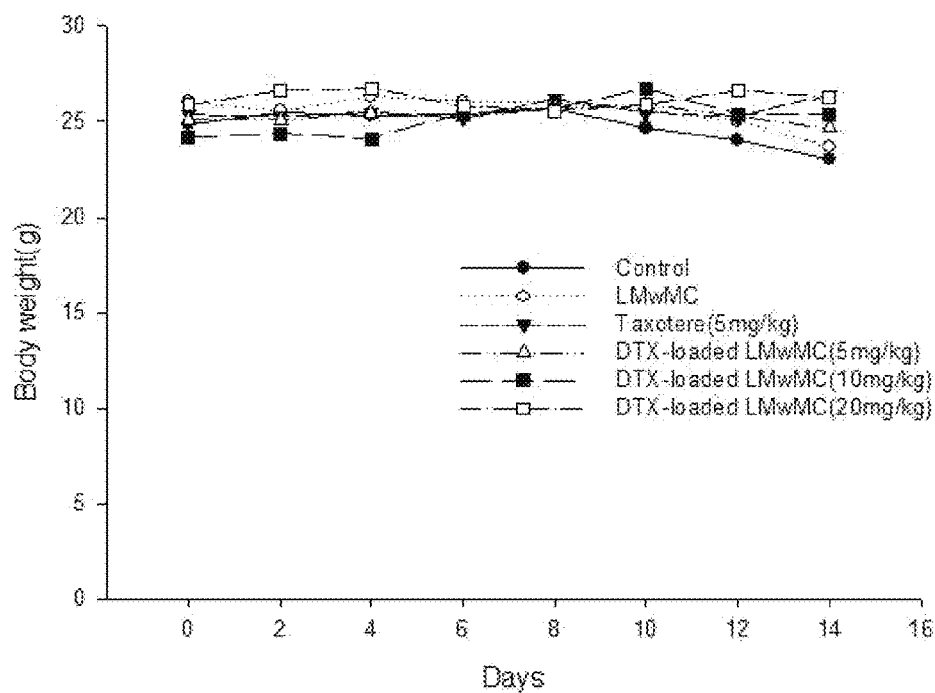
FIG. 17 is a graph for determining a change in weight during 14 days after local injection (intratumoral injection) of a control group and a treatment group (micelle of Example 1) into tumors of tumor animal models.

As a result, a control group decreased in weight due to tumor-induced stress and in vivo injury as shown in FIG. 17. On the other hand, in the case of treatment groups (a formulation in which an anticancer drug is loaded in a low-molecular methyl cellulose micelle), a normal weight was maintained without any specific toxicity.

(4) Determination of Survival Rate

The survival rate was observed at a constant time (3:00 pm) every day for 22 days after intratumoral injection on day 0.

Figure 18:
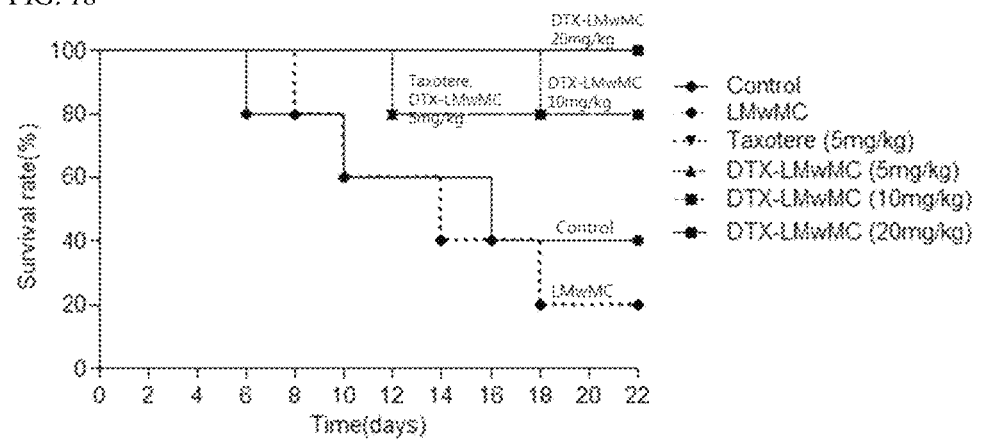
FIG. 18 is a graph showing a survival rate during 22 days after local injection (intratumoral injection) of a control group and a treatment group (micelle of Example 1) into tumors of tumor animal models.

As a result, 5, 10 and 20 mg/kg treatment groups (a formulation in which an anticancer drug is loaded in a low-molecular methyl cellulose micelle) showed a higher survival rate depending on the concentration as compared with the control group as shown in FIG. 18.

Example 6: Kidney Toxicity Test

In this study, 500 mg/kg, 250 mg/kg and 125 mg/kg administered groups were set as the medium and low dose administered groups, and a single intravenous administration toxicity experiment was performed on male mice to obtain the single intravenous administration toxicity data of the mice using MC having an average molecular weight of 8.5 kDa. The observation period was 2 weeks and clinical symptoms, a change in weight, autopsy findings of the kidney, a weight of the kidney, a histopathological change in the kidney were observed.

Figure 19:
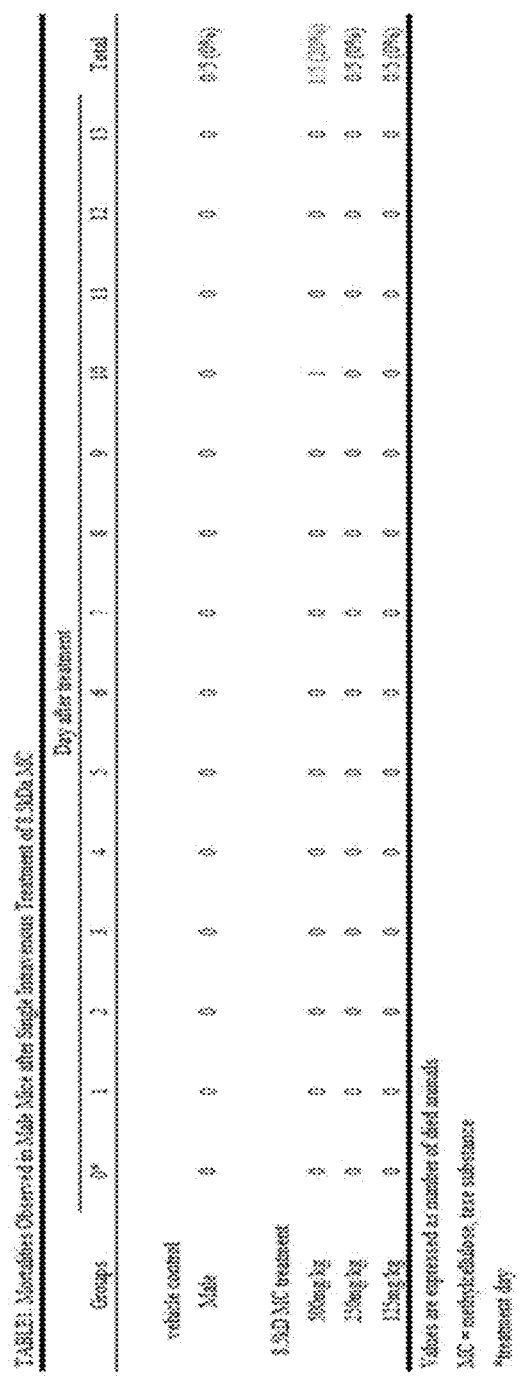
FIG. 19 is a table showing that, as a result of kidney toxicity test with respect to a low molecular weight methyl cellulose 125 mg/kg administered group of Preparation Example 1, there is no toxicity.

As a result of evaluation of single intravenous administration toxicity of the male mice using MC having an average molecular weight of 8.5 kDa, one case (⅕; 20%) of death occurred after 10 days of administration only in the case of the 8.5 kDa MC 500 mg/kg administered group, and death did not occur during the test period of 14 days in the case of 250 mg/kg and 125 mg/kg administered groups (FIG. 19).

Furthermore, the following Table 2 is a table summarizing the result of autopsy of organs after 2 weeks of intravenous injection, and each value refers to the number of animals with abnormalities observed/the total number of animals in the group (5/5 of the normal group refers to the number of normal animals/the total number of animals in the group). Particularly, autopsy findings such as renal discoloration and atrophy, and histopathological changes such as tubular necrosis and fibrosis were not determined in the 125 mg/kg administered group, indicating that there was no kidney toxicity activity.

TABLE 2

| Groups | Vehicle control Kidneys | Treated with 8.5 kDa-MC: 125 mg/kg |
| --- | --- | --- |
| Normal | 5/5 | 5/5 |
| DC-Atrophy | 0/5 | 0/5 |
| 1+ | 0/5 | 0/5 |
| 3+ | 0/5 | 0/5 |

*Degree = 1+: weak, 2+: medium, 3+: severe

Example 7: Determination of In Vivo Drug Efficacy of Low Molecular Weight Methyl Cellulose Micelle (Intravenous Injection)

(1) Preparation of Tumor Animal Model

B16F10 melanoma cells grown in an environment of 5% $CO_2$ and 37° C. were injected into 6-week-old male C57BL/6 mice.

First, after the mice were anesthetized with 50 μl of an anesthetic prepared by mixing 100 mg/kg of ketamine with 10 mg/kg of xylazine, B16F10 melanoma cells were injected subcutaneously in the left rear flank of the mice to prepare tumor animals. When the volume of the tumor reached ~100 mm³, the tumor animals were divided into 4 groups.

(2) Intravenous Injection and Identification of Tumor Size

The day when the tumor animals were divided into 4 groups when a tumor volume reached ~100 mm³ after preparation of the tumor animal models was defined as day 0. 100 μl of intravenous injection was injected at a time unlike intratumoral injection, and 4 mice per group were injected at a fixed time (3:00 pm) for a total of 5 times for 2 weeks at 3-day intervals from day 0. 100 μl of PBS was injected intratumorally 5 times at 3-day intervals for 2 weeks in a control group and 100 μl of PBS having 4 mg of low molecular weight methyl cellulose containing no drug were injected intratumorally 5 times at 3-day intervals for 2 weeks in a LMwMC group. 100 μl of solution (3.125 μl of Tween 80, 3.125 μl of ethanol and 93.75 μl of PBS) containing 0.1 mg of DTX was injected intratumorally 5 times at 3 day intervals for 2 weeks in a Taxotere group. 100 μl of a solution prepared at a ratio of 3.125% of Tween 80, 3.125% of ethanol and 96.75% of PBS and including 0.1 mg of docetaxel was injected intratumorally 5 times at 3 day intervals for 2 weeks. The prepared 1 mg-DTX loaded LMwMC powder was dissolved in 1,000 μl of PBS and 100 μl of the mixture per mouse was injected intratumorally 5 times at 3 day intervals for 2 weeks in a DTX-loaded LMwMC (5 mg/kg) group. To identify the size of tumors in mice, the mice were fixed by grabbing the tails of the mice at 3-day intervals for a total of 14 days like the case of intravenous injection, the size of the tumor in the left posterior flank was measured using a vernier caliper. The size of the tumor in the mouse was measured using a major axis of the vernier caliper with a graduation of 1 mm. After the long axis and short axis of the tumor were measured, the volume of the tumor was measured by the following Equation 3.

$$\text{Volume of tumor (mm}^3\text{)} = \frac{1}{2}ab^2 \qquad [\text{Equation 3}]$$

($a$: long axis, $b$: short axis)

Figure 20:
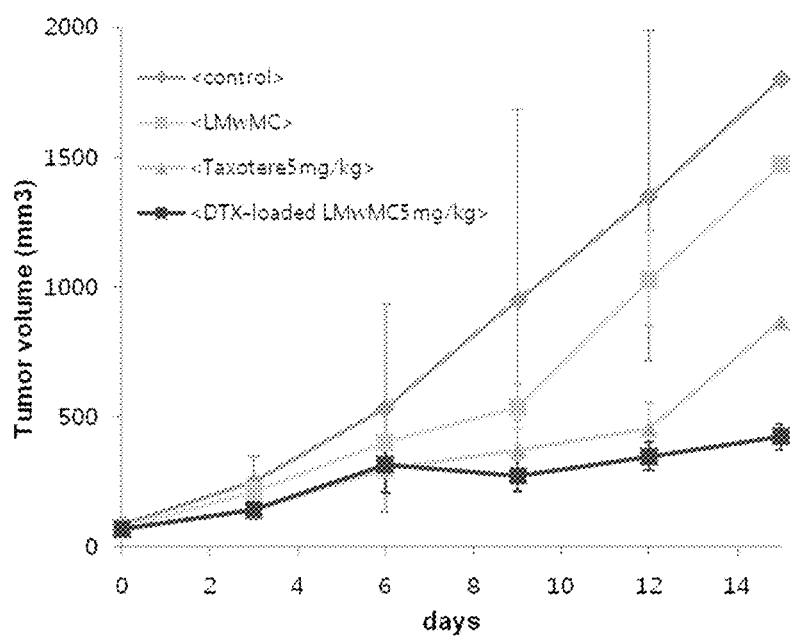
FIG. 20 is a graph showing a tumor size during 14 days after intravenous injection of a control group and a treatment group (micelle of Example 1) into tumor animal models.

The data of FIG. 20 indicates the average value of tumor sizes of 4 animals for each group.

Figure 22:
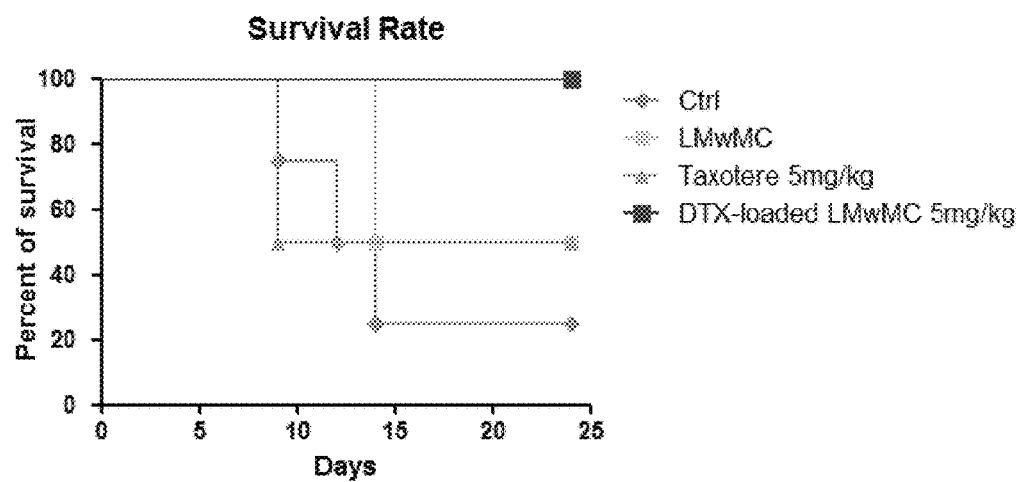
FIG. 22 is a graph showing a survival rate during 25 days after intravenous injection of a control group and a treatment group (micelle of Example 1) into tumor animal models.

As a result, as shown in FIG. 20, a formulation in which an anticancer drug is loaded in a low molecular weight methyl cellulose micelle was determined to show an excellent anti-cancer effect as compared with a control group and even when compared with Taxotere which is an existing DTX medicine. Further, as shown in FIG. 22, a low survival rate was observed even with the anticancer effect due to severe self-toxicity in the Taxotere group.

(3) Determination of Change in Weight

Each mouse was placed on an electronic scale for a total of 14 days at 3-day intervals, and the measured value was observed as in the case of intravenous injection.

Figure 21:
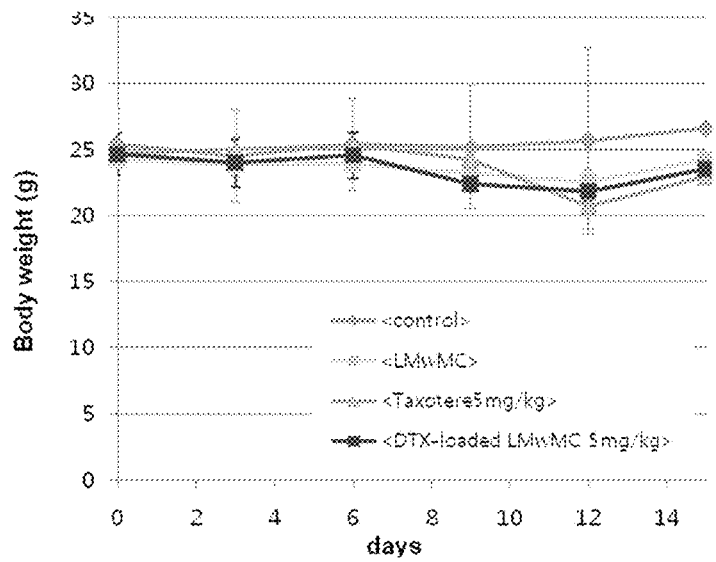
FIG. 21 is a graph showing a change in weight during 14 days after intravenous injection of a control group and a treatment group (micelle of Example 1) into tumor animal models.

As a result, approximately 15% of the weight was decreased due to self-toxicity in the Taxotere group as shown in FIG. 21. On the other hand, in the case of the treatment groups (a formulation in which an anticancer drug is loaded in a low-molecular methyl cellulose micelle), a normal weight was maintained without any specific toxicity.

(4) Determination of Survival Rate

The survival rate was observed at a constant time (3:00 pm) every day after intravenous injection on day 0.

As a result, all mice survived during the observation period in the treatment groups as compared to the high mortality due to the toxicity of the Taxotere group as shown in FIG. 22.

Accordingly, it was determined that the DTX-loaded LMwMC group showed lower toxicity and a higher anti-cancer effect than the Taxotere group.

The parenteral bioactive substance delivery system according to the present invention is used for solubilization based on only methyl cellulose unlike the conventional method of adding oil or other additives to solubilize a poorly soluble substance, and has no toxicity problem to have excellent biocompatibility, and biodegradability, and the desired bioactive substance may be delivered in vivo without side effects. Therefore, the low molecular weight methyl cellulose of the present invention can be used as a new bioactive substance delivery material for solubilizing a poorly soluble substance.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An external agent for skin, comprising methyl cellulose having a weight average molecular weight of 6 to 9.5 kDa in the form of a micelle, and a bioactive substance;
   wherein the micelle has a core-shell structure,
   wherein the core is formed by a hydrophobic block of a methoxide group and the shell is formed by a hydrophilic block of a hydroxyl group;
   wherein the bioactive substance is a drug, a vaccine, a protein, a peptide, a hormone, a nucleic acid or a gene construct, and
   wherein the methyl cellulose and the bioactive substance are contained in weight ratio of 20:1.

2. An external agent for skin, according to claim 1, wherein the methyl cellulose has a weight average molecular weight of 8.5 kDa.

3. A sustained release parenteral bioactive substance delivery composition, comprising methyl cellulose having a weight average molecular weight of 6 to 9.5 kDa in the form of a micelle, and a bioactive substance;
   wherein the micelle has a core-shell structure,
   wherein the core is formed by a hydrophobic block of a methoxide group and the shell is formed by a hydrophilic block of a hydroxyl group;
   wherein the bioactive substance is a drug, a vaccine, a protein, a peptide, a hormone, a nucleic acid or a gene construct, and
   wherein the methyl cellulose and the bioactive substance are contained in weight ratio of 20:1.

4. The composition according to claim 3, wherein the methyl cellulose has a weight average molecular weight of 8.5 kDa.

5. The composition according to claim 3, wherein the parenteral composition is intramuscular, intraperitoneal, intraabdominal, subcutaneous, intravenous or intraarterial.

6. A drug delivery system comprising methyl cellulose having a weight average molecular weight 6 to 9.5 kDa, and a drug,
   wherein the drug is carried in the micelle formed by the methyl cellulose of the drug delivery system,
   wherein the micelle has a core-shell structure, and
   wherein the core is formed by a hydrophobic block of a methoxide group and the shell is formed by a hydrophilic block of a hydroxyl group; and
   wherein the methyl cellulose and the drug are contained in weight ratio of 20:1.

7. The drug delivery system according to claim 6, wherein the methyl cellulose has a weight average molecular weight of 8.5 kDa.

8. The drug delivery system according to claim 6, wherein the drug is a poorly soluble drug, a hydrophilic drug, a protein drug or a nucleic acid-based drug.

9. The drug delivery system according to claim 6, wherein, when the micelle is formed in an aqueous solution and the drug is docetaxel, a loading rate of the drug satisfies Equation 1 below and is 60 to 90%;

Drug loading rate (%)=Total amount of drug in solubilized aqueous solution/Amount of initially injected drug×100. [Equation 1]

* * * * *